US007465538B2

(12) United States Patent
Watkins et al.

(10) Patent No.: US 7,465,538 B2
(45) Date of Patent: *Dec. 16, 2008

(54) MULTIPLEX FLOW ASSAYS PREFERABLY WITH MAGNETIC PARTICLES AS SOLID PHASE

(75) Inventors: Michael I. Watkins, Vacaville, CA (US); Richard B. Edwards, Cold Spring, NY (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/502,117

(22) Filed: Aug. 9, 2006

(65) Prior Publication Data

US 2006/0269962 A1 Nov. 30, 2006

Related U.S. Application Data

(60) Continuation of application No. 11/179,834, filed on Jul. 11, 2005, now Pat. No. 7,205,160, which is a division of application No. 10/734,957, filed on Dec. 11, 2003, now Pat. No. 6,960,478, which is a division of application No. 09/905,338, filed on Jul. 13, 2001, now Pat. No. 6,872,578, which is a division of application No. 09/302,920, filed on Apr. 30, 1999, now Pat. No. 6,280,618, and a continuation-in-part of application No. 08/972,563, filed on Nov. 18, 1997, now abandoned.

(51) Int. Cl.
*G01N 33/553* (2006.01)
*B32B 5/16* (2006.01)
*C12Q 1/70* (2006.01)

(52) U.S. Cl. .......................... 435/5; 428/402; 428/402.2; 428/402.22; 428/402.24; 428/403; 436/526; 435/7.22

(58) Field of Classification Search .................. None
See application file for complete search history.

(56) References Cited

U.S. PATENT DOCUMENTS

| | | | |
|---|---|---|---|
| 4,115,534 A | 9/1978 | Ithakissios | |
| 4,141,687 A | 2/1979 | Forrest et al. | |
| 5,091,206 A | 2/1992 | Wang et al. | |
| 5,242,964 A | 9/1993 | Bibette et al. | |
| 5,395,688 A | 3/1995 | Wang et al. | |
| 5,512,439 A | 4/1996 | Hornes et al. | |
| 5,561,070 A | 10/1996 | Stewart et al. | |
| 5,567,627 A | 10/1996 | Lehnen | |
| 5,601,983 A | 2/1997 | Takayama et al. | |
| 5,648,124 A | 7/1997 | Sutor | |
| 5,665,582 A | 9/1997 | Kausch et al. | |
| 5,840,587 A | 11/1998 | Stewart et al. | |
| 5,858,648 A * | 1/1999 | Steel et al. | ......... 435/5 |
| 6,013,531 A | 1/2000 | Wang et al. | |
| 6,023,540 A | 2/2000 | Walt et al. | |
| 6,449,562 B1 | 9/2002 | Chandler et al. | |
| 6,960,478 B2 | 11/2005 | Watkins et al. | |

FOREIGN PATENT DOCUMENTS

| | | |
|---|---|---|
| CA | 2072548 A1 | 12/1993 |
| DE | 4427821 A1 | 2/1996 |
| EP | 0 230 768 | 8/1987 |
| EP | 0965044 B1 | 3/2003 |
| GB | 1 561 042 | 2/1980 |
| GB | 1561042 | 2/1980 |
| JP | 61-132869 | 6/1986 |
| JP | 63-036151 | 2/1988 |
| JP | 05-093726 | 4/1993 |
| JP | 09-113512 | 5/1997 |
| WO | WO 89/11101 A1 | 11/1989 |
| WO | WO 90/07380 A2 | 7/1990 |
| WO | WO 97/14028 A2 | 4/1997 |
| WO | WO 97/35201 A1 | 9/1997 |

OTHER PUBLICATIONS

Condorelli, et al. Seroprevalence to some TORCH agents in a siciliam female polulation of fertile age. Eur. J. Epidemiol. May 1993:241-343.*

(Continued)

*Primary Examiner*—Mary E Mosher
*Assistant Examiner*—Stuart W Snyder
(74) *Attorney, Agent, or Firm*—Townsend and Townsend and Crew LLP

(57) ABSTRACT

Heterogeneous assays for different analytes in a single biological sample are performed simultaneously in a multiplexed assay that combines flow cytometry with the use of magnetic particles as the solid phase and yields an individual result for each analyte. The particles are distinguishable from each other by characteristics that permit them to be differentiated into groups, each group carrying an assay reagent bonded to the particle surface that is distinct from the assay reagents of particles in other groups. The magnetic particles facilitate separation of the solid and liquid phases, permitting the assays to be performed by automated equipment. Assays are also disclosed for the simultaneous detection of antibodies of different classes and a common antigen specificity or of a common class and different antigen specificities. Each type is accomplished by immunological binding at the surfaces of two distinct solid phases in a sequential manner with dissociation of the binding and washing of the solid phase in between the binding steps.

41 Claims, No Drawings

OTHER PUBLICATIONS

Blankenstein, Gert; "Microfabricated Flow System for Magnetic Cell and Particle Separation"; 1997, *Scientific and Clinical Applications of Magnetic Carriers*, pp. 233-245.

Harlow, et al., *Antibodies: A Laboratory Manual*, 1988, p. 353.

Melui et al.; Standardization of Protamine-Coated Microbeads Using Flow Cytometry for Heparin Quantitation; 1995, *Proceedings of the DGFZ Heidelberg Meetings*, 1 page abstract.

Odell, et al., *Principles of Competitive Protein-Binding Assays*, 2nd Ed., 1983, pp. 243-247.

Reseland, et al., *Chemical Abstracts*, Sep. 14, 1992, 117(11).

Scillian, James J. et al.; "Early Detection of Antibodies Against rDNA-Produced HIV Proteins With a Flow Cytometric Assay"; 1989, *Blood*, vol. 73, No. 7, pp. 2041-2048.

Spherotech, Inc. Catalog, table of contents and pp. 8-9 and 16-17, 1992-1993.

Stewart, M.W. et al.; Detection of Antiphospholipid Antibodies by Flow Cytometry: Rapid Detection of Antibody Isotype and Phospholipid Specificity; 1993, *Thrombosis and Haemostasis*, vol. 70, No. 4, pp. 603-607.

Vlieger, A.M. et al.; "Quantitation of Polymerase Chain Reaction Products by Hybridization-Based Assays with Fluorescent, Colorimetric, or Chemiluminescent Detection"; 1992, *Analytical Biochemistry*, vol. 205, pp. 1-7.

Wide, Leif; "Noncompetitive Versus Competitive Binding Assays"; 2003, *Competitive Binding Assays*, pp. 243-254.

Yang, Gang et al.; "Flow Cytometric Detection of Human Immunodeficiency Virus Type 1 Proviral DNA by the Polymerase Chain Reaction Incorporating Digoxigenin- or Fluorescein-Labeled dUTP"; 1995, *Cytometry*, vol. 21, pp. 197-202.

\* cited by examiner

MULTIPLEX FLOW ASSAYS PREFERABLY WITH MAGNETIC PARTICLES AS SOLID PHASE

CROSS REFERENCE TO RELATED APPLICATION

This application is a continuation of application Ser. No. 11/179,834, filed Jul. 11, 2005, now U.S. Pat. No. 7,205,160, which is a division of application Ser. No. 10/734,957 filed Dec. 11, 2003, now U.S. Pat. No. 6,960,478, which is a division of application Ser. No. 09/905,338 filed Jul. 13, 2001, now U.S. Pat. No. 6,872,578, which is a division of application Ser. No. 09/302,920 filed Apr. 30, 1999, now U.S. Pat. No. 6,280,618, which is a continuation-in-part of application Ser. No. 08/972,563, filed Nov. 18, 1997 now abandoned, the contents of all of which are incorporated herein by reference.

BACKGROUND OF THE INVENTION

1. Field of the Invention

This invention resides in the field of clinical assays indicative of biological conditions, and is of interest in the technology of binding assays for analytes in biological fluids for purposes of diagnosis, monitoring, or other clinical functions.

2. Description of the Prior Art

Since the initial disclosure of radioimmunoassays in 1961, a wide variety of in vitro assays using affinity-type binding have been developed. Variations include the type of binding (for example, specific vs. non-specific, and immunological vs. non-immunological), the type of detection (including the use of labels such as enzyme labels, radioactive labels, fluorescent labels, and chemiluminescent labels), methods of detecting whether or not binding has occurred (including methods in which bound species are separated from unbound species and methods that do not include such separation), and various other aspects of the assay procedure. The technology is currently used for the detection and quantitation of countless species, and serves as an analytical tool in the detection and monitoring of many physiological conditions and functions and the diagnosis and treatment of many diseases.

Improvements in the efficiency and reproducibility of these assays have been made by various developments including improved labels, methods of detection, automation, and systems for multiplex analyses. Each procedure however requires a sequence of steps, and any means of shortening the sequence, increasing the number of analyses that can be performed within a given period of time, or improving the reproducibility and versatility of the assay will benefit the purpose of the assay.

Many binding assays are heterogeneous assays, which rely in part on the transfer of analyte from a liquid sample to a solid phase by the binding of the analyte during the assay to the surface of the solid phase. At some stage of the assay, whose sequence varies depending on the assay protocol, the solid phase and the liquid phase are separated and the determination leading to detection and/or quantitation of the analyte is performed on one of the two separated phases. One type of solid phase that has been used are magnetic particles, which offer the combined advantages of a high surface area and the ability to be temporarily immobilized at the wall of the assay receptacle by imposition of a magnetic field while the liquid phase is aspirated, the solid phase is washed, or both. Descriptions of such particles and their use are found in Forrest et al., U.S. Pat. No. 4,141,687 (Technicon Instruments Corporation, Feb. 27, 1979); Ithakissios, U.S. Pat. No. 4,115,534 (Minnesota Mining and Manufacturing Company, Sep. 19, 1978); Vlieger, A. M., et al., Analytical Biochemistry 205:1-7 (1992); Dudley, Journal of Clinical Immunoassay 14:77-82 (1991); and Smart, Journal of Clinical Immunoassay 15:246-251 (1992).

Of further possible relevance to this invention is the state of the art relating to the use of flow cytometry for the detection and analysis of particles and species bound to the particles. Flow cytometry has been disclosed for use in the detection and separation of antigens and antibodies by Coulter Electronics Inc., United Kingdom Patent No. 1,561,042 (published Feb. 13, 1980); and for quantitation of PCR (Polymerase Chain Reaction) products by Vlieger, A. M., et al., Analytical Biochemistry 205:1-7 (1992). Flow cytometry has been limited in the analysis of biological samples. The sensitivity of those assay formats that do not require separation of free from bound species (i.e., sandwich and competitive assays) is adversely affected by the increased background signal noise caused by the unbound label. Antigen-capture antibody assays require the removal of non-specific immunoglobulin before the addition of class-specific labeled anti-Ig. Samples containing particulates (such as stool samples, for example) require the removal of this debris which would otherwise interfere with the flow cytometric measurement. Traditional separation techniques, such as filtration or centrifugation would be successful in removing unbound label or non-specific Ig but would fail to remove interfering particulates from the patient sample. In addition, these traditional separation techniques are difficult and/or costly to automate. The use of magnetic particles and magnetism is a well known method and has been shown to be both efficient and cost-effective in automated diagnostic systems.

Of still further possible relevance to this invention is the state of the art relating to the detection of antibodies of distinct classes but with a single common antigen specificity. The detection of antibodies of a particular class separately from those of other classes (i.e., IgG as distinct from IgA, or IgM) is relevant to various diagnostic determinations. For example, during the course of infection by an antigen, the different antibody classes are raised at different times, the IgM antibodies generally arising first, and as the infection progresses, the IgM and IgA antibodies dropping in concentration while the IgG antibodies arise. Determination of the relative amounts of these antibody classes for a specific antigen can thus be used as a measure of the stage of the infection and of how recently the infected person has been exposed to a particular disease, which information is of value in deciding how best to treat the disease. Differentiation among the antibody classes can also serve as an indication of whether or not a particular disease is active at the time of the assay. Existing assays capable of this type of differentiation have involved the use of multiple fluorophores that are excited at a common wavelength but emit at different wavelengths, achieved for example through energy transfer. Unfortunately, the utility and accuracy of this approach is limited by overlapping emission spectra and imperfect energy transfer. The approach also suffers from a lack of sensitivity. Other approaches involve the use of blocking agents which often give rise to false positives and similar problems.

A related type of diagnostic assay is one that detects antibodies of a single class but of multiple antigen specificities. This type of assay is useful in various types of screening tests and in generalized determinations which offer the useful information of whether exposure has occurred and when, without distinguishing in terms of the particular nature of the exposure. In formation of this type is useful in determining whether a subject is susceptible to infection in general, and can generate this type of information from a single patient sample rather than requiring multiple samples. Existing assays for this type of differentiation use blocking agents to inactivate antibodies of particular classes. The unfortunate result of these blocking agents is that they often give rise to false positive results.

SUMMARY OF THE INVENTION

The present invention resides in various ways of performing multiplex assays that are capable of differentiating between analytes.

In one aspect, this invention combines multiplexing of heterogeneous binding assays of a single fluid sample by flow cytometry with the use of solid magnetic particles as the solid phase to facilitate the separation of solid and liquid phases. The magnetic particles have sizes that are microscopic (and hence termed "microparticles") and that are classifiable into groups according to distinguishable characteristics or differentiation parameters. The groups are substantially discrete (nonoverlapping), with the mean values of the distinguishing characteristics of adjacent groups sufficiently far apart to permit differentiation of each group from the others by conventional automated detection methods. An assay reagent is bonded to each particle, with substantially all particles within each group bearing the same assay reagent and with different assay reagents from one group to the next. The groups are thus distinguishable not only by their distinctive differentiation parameters for purposes of differentiation but also by the assay reagents bonded to the particles such that all particles in each group take part in a distinct binding assay, and do so in a selective manner relative to the assay reagents bonded to particles in other groups.

This aspect of the invention further resides in a combination of solid particles for use in the multiplex assay described in the preceding paragraph, the particles being of magnetically responsive material and having a particular detectable parameter that encompasses a range of values that differentiate the particles into two or more substantially discrete groups that are distinguishable by automated detection methods that are appropriate for the particular parameter. The particles bearing assay reagents bonded to their surfaces, with a distinct assay reagent for each group.

The magnetic character of the particles permits the automated separation of solid phase from liquid phase at a point in the sequence of the assay prior to the stage at which the particle groups are differentiated according to the differentiation parameter. The separation can serve any of a variety of purposes, including the removal of sample debris from the assay components, the removal of sample components that would otherwise contribute significantly to the background noise at the detection stage, the removal of competing binding members that are not the subject of any of the assays but would otherwise interfere with the results, and the removal of bound from unbound species such as labels, analytes, analyte binding members, and label-binding member conjugates. The particular function in any given assay or combination of assays will depend on the nature of the assay and the assay protocol.

In another aspect, this invention provides methods for the simultaneous yet individual detection of antibodies of different immunogloblin classes (IgG, IgA, IgM, etc.) that have a single common antigen specificity, and alternatively the simultaneous yet individual detection of antibodies of different antigen specificities that are of a single immunoglobulin class. Each of these methods involves immunological binding at the surfaces of two distinct solid phases with an intervening dissociation of the binding and appropriate washing steps. When detecting antibodies of different classes but the same antigen specificity, the first solid phase is coated with the common antigen, and the second solid phase is coated with an immunological binding member that is specific for one of the various antibody classes of interest. When detecting antibodies of different antigen specificities but the same class, the first solid phase is coated with the antibody that is specific for the antibody class of interest, and the second solid phase is coated with an immunological binding member that is specific for one of the various antigen specificities of interest. In each case, the second solid phase can be uniform in its reactivity and specificity, but may alternatively consist of two or more subgroups that are capable of differentiation from each other and each of which has a different specificity. This permits multiple determinations as well as differentiation. Thus, the various subgroups of the second solid phase can differ in terms of the antibody class that they are specific for (in the case of the first type of determination) or in terms of the antigen specificities of the antibodies that they capture. The differentiation may be according to any of various differentiation parameters.

These and other features and advantages of the invention will be more readily understood by the description that follows.

DETAILED DESCRIPTION OF THE INVENTION AND PREFERRED EMBODIMENTS

The term "magnetically responsive material" is used herein to denote a material that responds to a magnetic field. Magnetically responsive materials of interest in this invention include paramagnetic materials, ferromagnetic materials, ferrimagnetic materials, and metamagnetic materials. Paramagnetic materials are preferred. Examples are iron, nickel, and cobalt, as well as metal oxides such as $Fe_3O_4$, $BaFe_{12}O_{19}$, $CoO$, $NiO$, $Mn_2O_3$, $Cr_2O_3$, and $CoMnP$. Rather than constituting the entire microparticle, the magnetically responsive material is preferably only one component of the microparticle whose remainder consists of a polymeric material to which the magnetically responsive material is affixed and which is chemically derivatized to permit attachment of an assay reagent.

In aspects and embodiments of this invention that involve the use of solid magnetic microparticles, the quantity of magnetically responsive material in the microparticle is not critical and can vary over a wide range. The quantity can affect the density of the microparticle, however, and both the quantity and the particle size can affect the ease of maintaining the microparticle in suspension for purposes of achieving maximal contact between the liquid and solid phase and for facilitating flow cytometry. Furthermore, an excessive quantity of magnetically responsive material in the microparticles will produce autofluorescence at a level high enough to interfere with the assay results. It is therefore preferred that the concentration of magnetically responsive material be low enough to minimize any autofluorescence emanating from the material. With these considerations in mind, the magnetically responsive material in a microparticle in accordance with this invention preferably ranges from about 1% to about 75% by weight of the particle as a whole. A more preferred weight percent range is from about 2% to about 50%, a still more preferred weight percent range is from about 3% to about 25%, and an even more preferred weight percent range is from about 5% to about 15%. The magnetically responsive material can be dispersed throughout the polymer, applied as a coating on the polymer surface or as one of two or more coatings on the surface, or incorporated or affixed in any other manner that secures the material in the polymer matrix.

When a solid phases consisting of microparticles is used, the polymeric matrix that forms the microparticle can be any material that can be formed into a microparticle and that bears certain other characteristics that make it useful in these assays. One such characteristic is that the matrix be inert to the components of the biological sample and to the assay reagents other than the assay reagent that is affixed to the microparticle. Other characteristics are that the matrix have minimal autofluorescence, that it be solid and insoluble in the sample and in any other solvents or carriers used in the assay, and that it be capable of affixing an assay reagent to the microparticle. Examples of suitable polymers are polyesters, polyethers, polyolefins, polyalkylene oxides, polyamides, polyurethanes, polysaccharides, celluloses, and polyisoprenes. Crosslinking is useful in many polymers for imparting structural integrity and rigidity to the microparticle. These considerations are also applicable to aspects and embodiments of this invention in which a solid phase other than microparticles is used.

Functional groups for attachment of the assay reagent can be incorporated into the polymer structure by conventional means, including the use of monomers that contain the functional groups, either as the sole monomer or as a co-monomer. Examples of suitable functional groups are amine groups ($—NH_2$), ammonium groups ($—NH_3^+$ or $—NR_3^+$), hydroxyl groups (—OH), carboxylic acid groups (—COOH), and isocyanate groups (—NCO). Useful monomers for introducing carboxylic acid groups into polyolefins, for example, are acrylic acid and methacrylic acid.

Attachment of the assay reagent to the solid phase surface can be achieved by electrostatic attraction, specific affinity interaction, hydrophobic interaction, or covalent bonding. Covalent bonding is preferred. Linking groups can be used as a means of increasing the density of reactive groups on the solid phase surface and decreasing steric hindrance to increase the range and sensitivity of the assay, or as a means of adding specific types of reactive groups to the solid phase surface to broaden the range of types of assay reagents that can be affixed to the solid phase. Examples of suitable useful linking groups are polylysine, polyaspartic acid, polyglutamic acid and polyarginine.

In embodiments in which microparticles are used as the solid phase and detection is performed by flow cytometry, care should be taken to avoid the use of particles that emit high autofluorescence since this renders them unsuitable for flow cytometry. Particles created by standard emulsion polymerization techniques from a wide variety of starting monomers generally exhibit low autofluorescence. Conversely, particles that have been modified to increase porosity and therefore surface area (such particles are referred to in the literature as "macroporous" particles) exhibit high autofluorescence. Autofluorescence in such particles further increases with increasing size and increasing percentage of divinylbenzene monomer.

Within these limitations, the size range of the microparticles can vary and particular size ranges are not critical to the invention. In most cases, the aggregated size range of the microparticles lies within the range of from about 0.3 micrometers to about 100 micrometers in particle diameter, and preferably within the range of from about 0.5 micrometers to about 40 micrometers.

Multiplexing with the use of microparticles in accordance with this invention is achieved by assigning the microparticles to two or more groups, each group performing a separate assay and separable from the other group(s) by a "differentiation parameter," which term is used herein to denote a distinguishable characteristic that permits separate detection of the assay result in one group from that in another group. One example of a differentiation parameter that can be used to distinguish among the various groups of particles is the particle size. The groups in this example are defined by nonoverlapping subranges of size. The particles fall into two or more such subranges, and in most cases the subranges will number from two to 100, each selectively active in a single assay and inert relative to the other assays simultaneously being performed or detected.

The widths of the size subranges and the spacing between mean diameters of adjacent subranges are selected to permit differentiation of the subranges by flow cytometry, and will be readily apparent to those skilled in the use of and instrumentation for flow cytometry. In this specification, the term "mean diameter" refers to a number average diameter. In most cases, a preferred subrange width is about ±5% CV or less of the mean diameter, where CV is the coefficient of variation and is defined as the standard deviation of the particle diameter divided by the mean particle diameter times 100 percent. The minimum spacing between mean diameters among the various subranges can vary depending on the microparticle size distribution, the ease of segregating microparticles by size for purposes of attaching different assay reagents, and the type and sensitivity of the flow cytometry equipment. In most cases, best results will be achieved when the mean diameters of different subranges are spaced apart by at least about 6% of the mean diameter of one of the subranges, preferably at least about 8% of the mean diameter of one of the subranges and most preferably at least about 10% of the mean diameter of one of the subranges. Another preferred subrange width relation is that in which the standard deviation of the particle diameters within each subrange is less than one third of the separation of the mean diameters of adjacent subranges.

Another example of a differentiation parameter that can be used to distinguish among the various groups of particles is fluorescence. Differentiation is accomplished by incorporating various fluorescent materials in the particles, the various fluorescent materials having different fluorescent emission spectra and being distinguishable on this basis.

Fluorescence can in fact be used both as a means of distinguishing the groups from each other and as a means of detection for the assay performed on the particle. The use of fluorescent materials with different emission spectra can be used as a means of distinguishing the groups from each other and as a means of distinguishing the group classification from the assay detections. An example of a fluorescence substance that can be used as a means of distinguishing groups is fluorescein and an example of a substance that can be used for the assay detection is phycoerythrin. Different particle groups are dyed with differing concentrations of fluorescein and assay-specific reporters are labeled with phycoerythrin.

Still other examples of a differentiation parameter that can be used to distinguish among the various groups of particles are light scatter, light emission, or combinations of light scatter and emission. Side angle light scatter varies with particle size, granularity, absorbance and surface roughness, while forward angle light scatter is mainly affected by size and refractive index. Thus, varying any of these qualities can serve as a means of distinguishing the various groups. Light emission can be varied by incorporating fluorescent materials in the microparticles and using fluorescent materials that have different fluorescence intensities or that emit fluorescence at different wavelengths, or by varying the amount of fluorescent material incorporated. By using a plurality of fluorescent emissions at various wavelengths, the wavelength difference can be used to distinguish the particle groups from each other and also to distinguish the labels indicating the occurrence of binding reactions in the assay from the labels that identify the particle groups.

In a preferred embodiment, the microparticles will have two or more fluorochromes incorporated within them so that each microparticle in the array will have at least three distinguishable parameters associated with it, i.e., side scatter together with fluorescent emissions at two separate wavelengths. For example, the microparticle can be made to contain a red fluorochrome such as Cy5 together with an orange fluorochrome such as Cy5.5. Additional fluorochromes can be used to further expand the system. Each microparticle can thus contain a plurality of fluorescent dyes at varying wavelengths.

Still another example of a differentiation parameter that can be used to distinguish among the various groups of particles is absorbance. When light is applied to microparticles the absorbance of the light by the particles is indicated mostly by the strength of the laterally (side-angle) scattered light while the strength of the forward-scattered light is relatively unaffected. Consequently, the difference in absorbance between various colored dyes associated with the microparticles is determined by observing differences in the strength of the laterally scattered light.

A still further example of a differentiation parameter that can be used to distinguish among the various groups of particles is the number of particles in each group. The number of particles of each group in an assay is varied in a known way, and the count of particles having various assay responses is determined. The various responses are associated with a particular assay by the number of particles having each response.

As the above examples illustrate, a wide array of parameters or characteristics can be used as differentiation parameters to distinguish the microparticles of one group from those of another. The differentiation parameters may arise from particle size, from particle composition, from particle physical characteristics that affect light scattering, from excitable fluorescent dyes or colored dyes that impart different emission spectra and/or scattering characteristics to the microparticles, or from different concentrations of one or more fluorescent dyes. When the distinguishable microparticle parameter is a fluorescent dye or color, it can be coated on the surface of the microparticle, embedded in the microparticle, or bound to the molecules of the microparticle material. Thus, fluorescent microparticles can be manufactured by combining the polymer material with the fluorescent dye, or by impregnating the microparticle with the dye. Microparticles with dyes already incorporated and thereby suitable for use in the present invention are commercially available, from suppliers such as Spherotech, Inc. (Libertyville, Ill., USA) and Molecular Probes, Inc. (Eugene, Oreg., USA). A list of vendors of flow cytometric products can be found on the Internet at www.molbio.princeton.edu/facs/FCMsites.html.

The type of assay reagent attached to the microparticle surface for any single group of microparticles will vary depending on both the analyte and the type of assay. The assay reagent can be a binding agent with specific affinity for the analyte, or a binding agent with affinity for a narrow range of species that includes the analyte but excludes other analytes whose assays are performed by contact with other microparticle subranges, or any binding species in general that will selectively engage in the assay for a single analyte to the exclusion of the others. Examples of assay reagents are antibodies, antigens or haptens, and other types of proteins with binding specificity such as avidin and biotin.

Another type of assay reagent that can be attached to the microparticle surface for any single group of microparticles is the analyte itself. In the analysis, the attached analyte will compete with a narrow range of species in the sample that also includes analyte. Examples of these assay reagents are antibodies, antigens and haptens.

The assay performed at the surfaces of microparticles within a single group of particles can be any type of heterogeneous assay that yields a result differentiating a certain analyte from others in the sample.

Competitive assays, for example, can be performed by using magnetically responsive microparticles to which are bound molecules of a binding protein (such as an antibody) specific for the analyte. During the assay, the sample and a quantity of labeled analyte, either simultaneously or sequentially, are mixed with the microparticles. By using a limited number of binding sites on the microparticles, the assay causes competition between the labeled analyte and the analyte in the sample for the available binding sites. After a suitable incubation period, the mixture of liquid and solid is placed under the influence of a magnetic field, causing the microparticles to adhere to the walls of the reaction vessel, and the liquid phase is removed. The microparticles, still adhering to the vessel wall, are then washed to remove any remaining unbound analyte and label, and resuspended in a carrier liquid for introduction into a flow cytometer where the microparticles are classified by size and the label detected. An example of an analyte that is readily detected in this manner is vitamin $B_{12}$. A useful particle-bound assay reagent for this analyte is intrinsic factor, and a competing label-bound analyte is $B_{12}$ covalently linked to phycoerythrin.

Immunometric or sandwich assays, as another example, are performed by using magnetically responsive microparticles to which are bound antibodies to the analyte. In this case, the bound antibodies are present in excess relative to the suspected quantity range of the analyte so that all of the analyte binds. The microparticles are placed in contact with the sample, and simultaneously or sequentially, a second antibody to same analyte is added, again in excess relative to the analyte, the first and second antibodies binding different epitopes on the analyte in a non-interfering manner, and the second antibody being conjugated to a detectable label. After a suitable incubation period, the liquid mixture with microparticles suspended therein is placed under the influence of a magnetic field, causing the microparticles to adhere to the walls of the reaction vessel, and the liquid phase is removed. The microparticles, still adhering to the vessel wall, are then washed to remove excess amounts of the second, labeled antibody that have not become bound to the immobilized analyte, and the microparticles are then resuspended in a carrier liquid for introduction into a flow cytometer where they are sorted by size and the label detected. An example of an analyte that is readily detected in this manner is thyroid stimulating hormone (TSH). The label on the second antibody can again be phycoerythrin.

This invention can also be applied to assays that do not separate bound label from unbound label but nevertheless require separation of the solid from the liquid phase at some point in the assay. Examples are assays for identifying antibodies to infectious disease agents. The analyte antibodies are members of one of several possible immunoglobulin classes, and it is medically useful to know which class is present among the antibodies to the target antigen. The analyte antibodies bind to particle-bound antigen in the assay, and are followed by labeled antibodies to the human immunoglobulin class of interest. In order to prevent such labeled antibodies from reacting with members of the immunoglobulin class that are not directed at the disease antigen, it is necessary to remove the sample from the particles thereby removing the non-specific immunoglobulins. The magnetic particles serve this purpose as in the assays described in the preceding paragraphs, and this is performed before the label is added.

A different type of serological assay for antibodies are a further example, performed by using magnetically responsive microparticles to which are bound antibodies to the immunoglobulin class of the antibody analyte. The microparticles are placed in contact with the sample. After a suitable incubation period, the liquid mixture with suspended microparticles is placed under a magnetic field to adhere the microparticles to the reaction vessel walls, and the liquid phase is removed. Labeled antigen is then added to the vessel containing the microparticles, the antigen being the one that the analyte antibodies are directed towards and that is conjugated to a detectable label or is attached through other binding pairs. After a suitable incubation period, this new liquid mixture is introduced into a flow cytometer where the microparticles are classified by the differentiation parameter and the label detected. An example of an analyte susceptible to this type of assay is human anti-Rubella IgM. The particle-bound reagent is anti-human IgM antibody and the labeled reagent is Rubella antigen.

The multiple assays that can be performed on a single fluid sample in accordance with this invention can be all of the same type (i.e., all competitive, all immunometric, all serological, etc.) or a combination of different types. Examples of combinations of assays that can be performed by this method are:

(1) Assays for thyroid stimulating hormones and either free $T_4$ or total $T_4$;
(2) Assays for vitamin $B_{12}$ and folate; and
(3) ToRCH assays, detecting serum IgG antibodies to Toxoplasma gondii, Rubella virus, Cytomegalovirus, and Herpes Simplex Virus Types 1 and 2.

Methods of and instrumentation for flow cytometry are known in the art, and those that are known can be used in the practice of the present invention. Flow cytometry in general resides in the passage of a suspension of the microparticles as a stream past a light beam and electro-optical sensors, in such a manner that only one particle at a time passes through the region. As each particle passes this region, the light beam is perturbed by the presence of the particle, and the resulting scattered and fluorescent light are detected. The optical signals are used by the instrumentation to identify the subgroup to which each particle belongs, along with the presence and amount of label, so that individual assay results are achieved. Descriptions of instrumentation and methods for flow cytometry are found in the literature. Examples are McHugh, "Flow Microsphere Immunoassay for the Quantitative and Simultaneous Detection of Multiple Soluble Analytes," *Methods in Cell Biology* 42, Part B (Academic Press, 1994); McHugh et al., "Microsphere-Based Fluorescence Immunoassays Using Flow Cytometry Instrumentation," *Clinical Flow Cytometry*, Bauer, K. D., et al., eds. (Baltimore, Md., USA: Williams and Williams, 1993), pp. 535-544; Lindmo et al., "Immunometric Assay Using Mixtures of Two Particle Types of Different Affinity," *J. Immunol. Meth.* 126: 183-189 (1990); McHugh, "Flow Cytometry and the Application of Microsphere-Based Fluorescence Immunoassays," *Immunochemica* 5: 116 (1991); Horan et al, "Fluid Phase Particle Fluorescence Analysis: Rheumatoid Factor Specificity Evaluated by Laser Flow Cytophotometry," *Immunoassays in the Clinical Laboratory*, 185-189 (Liss 1979); Wilson et al., "A New Microsphere-Based Immunofluorescence Assay Using Flow Cytometry," *J. Immunol. Meth.* 107: 225-230 (1988); Fulwyler et al., "Flow Microsphere Immunoassay for the Quantitative and Simultaneous Detection of Multiple Soluble Analytes," *Meth. Cell Biol.* 33: 613-629 (1990); Coulter Electronics Inc., United Kingdom Patent No. 1,561,042 (published Feb. 13, 1980); and Steinkamp et al., *Review of Scientific Instruments* 44(9): 1301-1310 (1973).

Similarly, methods of and instrumentation for applying and removing a magnetic field as part of an automated assay are known to those skilled in the art and reported in the literature. Examples of literature reports are the Forrest et al. patent, the Ithakissios patent, the Vlieger et al. paper, the Dudley paper and the Smart paper, all referenced above in the Description of the Prior Art. All of the citations in this and the preceding paragraph are incorporated herein by reference.

As noted above, one aspect of this invention resides in assays for the simultaneous yet individual detection of antibodies of different classes that have a single common antigen specificity. These assays are conducted by first contacting the sample with a solid phase whose surface bears the antigen whose specificity is common to the antibodies being detected. This will result in the capture of all classes of antibodies with specific binding affinity towards that antigen. The solid phase is then separated from the sample and washed to remove unbound materials, which may include antibodies with other specificities and/or other extraneous sample components. The washed solid phase is then placed in contact with a liquid medium and the captured antibodies are released into the medium by deactivation of the immunological binding. A supernatant is thereby formed that contains antibodies of different immunoglobulin classes but the same antigen specificity. The supernatant is then placed in contact with a second solid phase. The second solid phase is in one or more portions, each portion bearing antibodies on its surface that are specific to a particular immunoglobulin class. Thus, one portion bears anti-IgG antibodies on its surface, another bears anti-IgM antibodies, and still others bear anti-IgA antibodies and/or antibodies specific for other classes. The solid phase may consist of only one of these portions or two or more. When two or more such portions are present, the portions are distinguishable from each other in a manner permitting differentiation between them so that independent determinations can be made without separating the portions. This is accomplished by using any of the "differentiation parameters" described above in connection with other aspects of this invention. Once these antibodies are captured by the second solid phase, the presence of the antibodies on the second solid phase surface is detected by contacting the second solid phase with labeled binding members that have a specific binding affinity toward the captured antibodies. Thus, class-specific antibodies, for example IgG-specific, IgA-specific, and IgM-specific antibodies, all labeled, can be used, or alternatively, labeled antigen can be used. The presence of the label and, if desired, its amount can then be determined by conventional means.

As further noted above, the invention also resides in assays for the simultaneous yet individual detection of antibodies of different antigen specificities but a common immunoglobulin class. These assays are begun by contacting sample with a solid phase coated with an antibody that is specific for the immunoglobulin class of interest. This will result in the capture of antibodies of that immunoglobulin class regardless of their antigen specificity. The solid phase is then separated from the sample and washed to remove unbound materials, which may include antibodies of other immunoglobulin classes and/or extraneous sample components. The washed solid phase is then placed in contact with a liquid medium and the captured antibodies are released into the medium by deactivation of the immunological binding. The supernatant thus contains antibodies of the single selected class but different antigen specificities. The supernatant is then placed in contact with a second solid phase, which is in one or more portions, each bearing immmunological binding members on its surface that are specific for antibodies of a single antigen specificity. These immunological binding members are preferably the antigens themselves. Thus, when more than one portion is used, different portions will bear different antigens on their surfaces. Likewise, when more than one portion is used, the portions will be distinguishable from each other in a manner permitting differentiation between them so that independent determinations can be made without separating the portions. Here again, any of the "differentiation parameters" listed above may be used. Once the antibodies are captured by the second solid phase, their presence on the surface of the second solid phase is detected by contacting the second solid phase with a labeled antibody that is specific for the common immunological class.

In the assays described in the preceding two paragraphs, either or both of the first and second solid phases of each assay may be particles or any other size, shape or configuration of solid material, including test tube walls, dipsticks and the like. Microparticles are of particular interest, and magnetic microparticles are preferred. Microparticles offer various options for the differentiation parameter as described above and are readily analyzed and differentiated by flow cytometry. Magnetic microparticles further provide the capability of separation from the liquid phases by magnetic fields. Magnetic separation is useful in the washing stage, and also in the recovery of the supernatant from the first solid phase after the captured antibodies have been released.

In both assays, the release of the captured antibodies from the antigen or antibody coating on the first solid phase is achieved by conventional means that will dissociate the binding interaction without irreversibly denaturing the antibody. This may be achieved for example by the use of a weak acid such as 0.1 M acetic acid. Other acids and methods will be readily apparent to those skilled in the art.

The detection steps in each of the various assays addressed by this invention may use any of the wide variety of detection methods used in immunological assays. Fluorescence by the use of fluorophore labels conjugated to one of the binding members is one means of detection that is widely used and applicable to these assays as well. When fluorophores are used, it is preferable to select a fluorophore that contributes as little autofluorescence as possible. The fluorophore phycoerythrin is preferred in this regard, since its extinction coefficient and quantum yield are superior to those of other fluorophores.

This invention is applicable to the analysis of biological fluids, notably physiological fluids such as whole blood, serum, urine, spinal fluid, saliva, and stool samples.

The following examples are offered strictly for purposes of illustration.

EXAMPLE 1

This example illustrates the attachment of viral antigen (Rubella (RUB), Cytomegalovirus (CMV) and Herpes Simplex Virus 2 (HSV2)) to magnetic beads.

Three types of magnetic beads were used:

SPHERO™ Carboxyl Magnetic particles, from Spherotech, Inc., Libertyville, Ill., USA—poly(styrene/acrylic acid particles), 4.35 micrometers (μm) in diameter, density 1.17 g/cc, containing 12% magnetite (by weight)

SPHERO™ Carboxyl Magnetic particles, from Spherotech, Inc., Libertyville, Ill., USA—poly(styrene/acrylic acid particles), 3.18 μm in diameter, density 1.17 g/cc, containing 12% magnetite (by weight)

SINTEF Applied Chemistry, Trondheim, Norway—poly(styrene/divinylbenzene) particles, 10 μm in diameter, density 1.23 g/cc, containing 17.9% magnetite/maghemite (by weight)

Table I lists the amounts of each of the materials used in this preparation:

TABLE I

| | | Amounts Used | | | |
|---|---|---|---|---|---|
| Bead | Viral Antigen | Amount of Beads | Weight of Viral Antigen | Volume of Viral Antigen | Volume of Phosphate Buffer (100 mM) |
| 4.35 μm | CMV | 10 mg | 225.8 μg | 322.6 μL | 677.4 μL |
| 3.18 μm | HDV2 | 5 mg | 163.0 μg | 815.0 μL | 185.0 μL |
| 10 μm | RUB | 5 mg | 5.2 μg | 104.0 μL | 896.0 μL |

The beads in each case were placed in test tubes and washed multiple times with 100 mM phosphate buffer, pH 6.8. The washed beads were then suspended in the volume of phosphate buffer listed in Table I, and respective antigen solution was added (CMV antigen from Chemicon International Incorporated, Temecula, Calif., USA; HSV2 antigen from Ross Southern Labs, Salt Lake City, Utah, USA; and RUB antigen from Viral Antigens, Memphis, Tenn., USA) in the amount listed in the Table. The test tubes were then rotated in end-over-end fashion overnight at room temperature. The tubes were then placed on a magnetic separator and the supernatant was drawn off and discarded. The resulting beads were washed with a wash buffer consisting of 50 mM phosphate buffer, pH 7.4, 0.01% Tween 20, 1% bovine serum albumin, 0.1% sodium azide, 150 mM sodium chloride, then again subjected to magnetic separation, and suspended in a storage buffer consisting of 50 mM phosphate buffer, pH 7.4, 5% glycerol, 1% bovine serum albumin, 0.1% sodium azide, 150 mM sodium chloride.

EXAMPLE 2

This example illustrates the use of the CMV-coated magnetic beads of Example 1 in a flow cytometric immunoassay.

Procedure:
1. 100 μL of Bio-Rad CMV IgG Immunoassay positive and negative controls (Bio-Rad Laboratories, Inc., Hercules, Calif., USA, diluted 1:10 in wash buffer) were added to 12×75 mm polypropylene test tubes.
2. To each tube was added 100 μL of the CMV antigen-coated particles (described in Example 1) diluted 1:1000 in wash buffer.
3. The tubes were vortexed at ambient temperature for 30 minutes.
4. After vortexing, 800 μL of wash buffer was added to each tube.
5. The tubes were placed in a magnetic separator for 3 minutes and the liquid phase removed.
6. Steps 4 and 5 are repeated but with 1000 μL of wash buffer.
7. 200 μL of a 1:100 dilution of anti human IgG-phycoerythrin conjugate (Chemicon International Inc., Temecula, Calif., USA) is added.
8. The tubes were vortexed at ambient temperature for 30 minutes.

9. After this time, the samples are injected into the flow cytometer (Bryte HS, Bio-Rad Laboratories, Inc., Hercules, Calif., USA) equipped with a Xenon arc lamp.

Results:

Positive and negative CMV controls exhibited fluorescent peaks corresponding to 898 and 60 relative linear fluorescence units, respectively. As expected, the positive control gave significantly elevated signal relative to that of the negative control.

EXAMPLE 3

This example illustrates the use of the CMV, HSV2 and RUB-coated magnetic particles of Example 1 in a simultaneous multi-analyte flow cytometric immunoassay.

Procedure:
1. 100 µL of patient samples (diluted 1:10 in wash buffer), of known CMV, HSV2 and RUB antibody status, were added to 12×75 mm polypropylene test tubes.
2. To each tube was added 100 µL of a mixture of CMV, HSV2 and RUB antigen-coated particles (described in Example 1) diluted in wash buffer.
3. The tubes were vortexed at ambient temperature for 15 minutes.
4. After vortexing, 800 µL of wash buffer was added to each tube.
5. The tubes were placed in a magnetic separator for 5 minutes and the liquid phase removed.
6. Steps 4 and 5 are repeated but with 1000 µL of wash buffer.
7. 200 µL of a 1:300 dilution of anti-human IgG-phycoerythrin conjugate (Chemicon International Inc., Temecula, Calif., USA) is added.
8. The tubes were vortexed at ambient temperature for 15 minutes.
9. After this time, the samples are injected into the flow cytometer (Bryte HS, Bio-Rad Laboratories, Inc., Hercules, Calif., USA) equipped with a Xenon arc lamp.

Results:

The results are summarized in Table II below:

TABLE II

Test Results

| Sample | Antibody Status | | | Relative Linear Fluorescence Units | | |
|--------|-----|------|-----|-----|------|-----|
|        | CMV | HSV2 | RUB | CMV | HSV2 | RUB |
| CN6    | +   | −    | +   | 14  | 7    | 155 |
| CN8    | +   | −    | +   | 16  | 6    | 181 |
| CN12   | −   | −    | +   | 5   | 7    | 240 |
| CN15   | −   | −    | +   | 5   | 6    | 329 |
| 23     | −   | +    | −   | 5   | 45   | 43  |

The data in Table II show that positive samples have substantially increased fluorescence relative to the negative samples.

EXAMPLE 4

This example illustrates the covalent attachment of rubella (RUB) antigen to magnetic beads.

The magnetic particles were SPHERO™ Carboxyl Magnetic particles, from Spherotech, Inc., Libertyville, Ill., USA—poly(styrene/alkylenic acid particles), 25 mg/mL, 7.1 micrometers in diameter, density 1.097 g/cc, containing 5% magnetite (by weight).

1.13 mL of beads were placed in a test tube and washed multiple times with 50 mM 2-(N-morpholino)ethanesulfonic acid (MES) buffer, pH 5.5. The washed beads were then suspended in 1.25 mL of 2 mg/mL polylysine (MW 18,000) in 50 mM MES buffer, pH 5.5. To the resulting solution was added 125 µL of 20 mg/mL 1-ethyl-3-(3-dimethyl-aminopropyl)carbodiimide (EDC) in water. The solution was placed on an end-over-end rotator at ambient temperature for 18 hours. After this time the solution was separated from the particles and discarded. The particles were then washed multiple times with 0.2M borate buffer, pH 8.5. The particles were resuspended in 2.5 mL of borate buffer, pH 8.5. To this solution was added 50 mg of succinic anhydride. The solution was then placed on an end-over-end rotator at ambient temperature for 4 hours. After this time the solution was separated from the particles and discarded. The particles were then washed multiple times with 50 mM MES, pH 5.5. The particles were washed twice with 0.1M carbonate buffer, pH 9.6 and then 3 times with 20 mM phosphate buffer, pH 4.5. The particles were finally suspended in 1 mL of 20 mM phosphate buffer, pH 4.5. To this solution was added 1 mL of 20 mg/mL EDC in 20 mM phosphate buffer, pH 4.5. The solution was then placed on an end-over-end rotator at ambient temperature for 4 hours. After this time the solution was separated from the particles and discarded. The particles were washed 3 times with 20 mM phosphate buffer, pH 4.5. Afterwards the beads were suspended in 2 mL of 0.2 M borate buffer, pH 8.5. To this was added 0.5 mL of 0.2 mg/mL of rubella antigen from Viral Antigens Incorporated, Memphis, Tenn., USA in 0.2M borate buffer, pH 8.5, 2 mg/mL 3-[(3-cholamidopropyl)dimethylammonio]-1-propane-sulfonate (CHAPS), 0.1% sodium azide. The test tube were then rotated in end-over-end fashion overnight at room temperature. The next day, 100 µL of 0.25M hydroxylamine in 0.2M borate buffer, pH 8.5 was introduced. The solution was then placed on an end-over-end rotator at ambient temperature for 1 hour. After this time the solution was separated from the particles and discarded. The particles were washed 3 times with wash buffer (see Example 1). The resulting beads were taken up in 2.5 mL of wash buffer and placed on an end-over-end rotator at ambient temperature for 1 hour. After this time the solution was separated from the particles and discarded. The particles were washed 3 times with storage buffer (see Example 1). Finally the particles were suspended in 1 mL of storage buffer and placed at 4° C.

EXAMPLE 5

This example illustrates the use of magnetic particles with covalently attached rubella antigen of Example 4 in a quantitative flow cytometric immunoassay.

Procedure:
1. 100 µL of Bio-Rad RUB IgG Immunoassay standards, high positive, low positive and negative controls (Bio-Rad Laboratories, Inc., Hercules, Calif., diluted 1:30 in wash buffer), were added to 12×75 mm polypropylene test tubes.
2. To each tube was added 100 µL of the RUB antigen-coated particles (described above) diluted 1:200 in wash buffer.
3. The tubes were vortexed at ambient temperature for 15 minutes.
4. After vortexing, 750 µL of wash buffer was added to each tube.

5. The tubes were placed in a magnetic separator for 1 minute and the liquid phase removed.
6. Steps 4 and 5 are repeated two more times but with 1000 µL of wash buffer.
7. 200 µL of a 1:300 dilution of anti human IgG-phycoerythrin conjugate (Chemicon International Inc., Temecula, Calif., USA) is added.
8. The tubes were vortexed at ambient temperature for 15 minutes.
9. The samples are then injected into the flow cytometer (Bryte HS, Bio-Rad Laboratories, Inc., Hercules, Calif., USA) equipped with a Xenon/Mercury arc lamp.

Results:

Table III contains data generated by following the above protocol. The standards were fitted to a 4-parameter logistic equation. The concentrations of all samples were calculated from this curve. The values for the controls are similar to the values assigned by the Bio-Rad ELISA technique.

TABLE III

Test Results

| Sample | Relative Linear Fluorescence Units | Observed [RUB] (IU/mL) | Reported [RUB] (IU/mL) |
|---|---|---|---|
| Standard 0 | 21 | 0 | 0 |
| Standard 1 | 101 | 6 | 8 |
| Standard 2 | 225 | 30 | 30 |
| Standard 3 | 464 | 115 | 96 |
| Standard 4 | 652 | 216 | 240 |
| Standard 5 | 1171 | 623 | 614 |
| High Positive | 580 | 174 | 135 |
| Low Positive | 175 | 18 | 14 |
| Negative | 33 | 0.3 | 0.5 |

EXAMPLE 6

This example illustrates the simultaneous yet individual detection of antibodies of two different immunoglobulin classes, both having a common antigen specificity. The antigen specificity is Rubella, and the two immunoglobulin classes are IgG and IgM.

A 10-µL sample was placed in a tube, and 100 µL of Rubella antigen-coated magnetic particles (0.9 µm in diameter) were added. The mixture was incubated for 16 minutes on a vortexer at room temperature. The particles were then washed once with 300 µL, and twice with 400 µL portions of a wash buffer, each time followed by vortexing, magnetic separation and aspiration. Acetic acid (100 µL, 0.1 M) was then added, and the mixture was incubated for 16 minutes on a vortexer at room temperature. Magnetic separation was again performed for one minute, and the supernatant was transferred to another tube. Potassium hydrogen phosphate ($K_2HPO_4$, 50 µL, 0.6 M) was then added, followed by 50 µL of a mixture of 7.1-µm diameter goat anti-hIgM-coated magnetic particles and 4.35-µm diameter magnetic particles coated with goat anti-hIgG (Fc specific, $F(ab')_2$ fragment) in Neonatal Calf Serum. The resulting mixture was incubated for 16 minutes on a vortexer at room temperature, followed by washing once with 200 µL, then twice with 400 µL portions of wash buffer. After a one-minute magnetic separation and aspiration, labeled class-specific antibodies were added, 100 µL of a mixture of anti-hIgM-phycoerythrin and anti-hIgG-phycoerythrin. The mixture was incubated for 16 minutes on a vortexer at room temperature, then washed once with 300 µL, then twice with 400 µL portions of wash buffer, vortexed and magnetically separated (one minute), then aspirated. The particles were suspended in wash buffer (150 µL), then read on the flow cytometer of the preceding examples.

The results in relative linear fluorescence units are listed in Table IV below.

TABLE IV

Test Results for Rubella Antibodies IgG and IgM

| Sample | IgG Value (IU/mL) | IgM Value (signal/-cutoff) | 4.35 µm Particle (IgG) Relative Linear Units | 7.10 µm Particle (IgM) Relative Linear Units |
|---|---|---|---|---|
| GW917 | 29.07 | 2.38 | 410.5 | 396.0 |
| GW22 | 253 | 0.947 | 403.2 | 89.0 |
| 66S | 0 | 0.534 | 80.2 | 63.5 |
| Diluent | | | 5.1 | 6.9 |
| Particles only | | | 2.2 | 3.2 |

The data in Table IV demonstrate that the positive samples (GW917 and GW22) gave significantly greater signals than the negative sample (66S).

EXAMPLE 7

This example illustrates the simultaneous yet individual detection of antibodies of a distinct antigen specificity and a single immunoglobulin class. The antigen specificity is the Rubella, and the immunoglobulin class is IgM.

A 10-µL sample was placed in a tube, and 100 µL of anti-human IgM-coated magnetic particles (0.9 µm in diameter) were added. The mixture was incubated for 16 minutes on a vortexer at room temperature. The particles were then washed once with 300 µL, and twice with 400 µL portions of a wash buffer, each time followed by vortexing, magnetic separation and aspiration. Acetic acid (100 µL, 0.1 M) was then added, and the mixture was incubated for 16 minutes on a vortexer at room temperature. Magnetic separation was again performed for one minute, and the supernatant was transferred to another tube. Potassium hydrogen phosphate ($K_2HPO_4$, 50 µL, 0.6 M) was then added, followed by 50 µL of a Rubella antigen-coated 7.1-µm diameter magnetic particles diluted 1:35 in Neonatal Calf Serum. The resulting mixture was incubated for 16 minutes on a vortexer at room temperature, followed by washing once with 200 µL, then twice with 400 µL portions of wash buffer. After a one-minute magnetic separation and aspiration, 100 µL of anti-hIgM was added. The mixture was incubated for 16 minutes on a vortexer at room temperature, then washed once with 300 µL, then twice with 400 µL portions of wash buffer, vortexed and magnetically separated (one minute), then aspirated. The particles were suspended in wash buffer (150 µL), then read on the flow cytometer of the preceding examples.

The results (in relative linear fluorescence units) are listed in Table V below.

TABLE V

Test Results for Rubella IgM Antibodies

| Sample | IgM Value (signal/-cutoff) | Relative Linear Units |
|---|---|---|
| GW22 | 0.947 | 10.5 |
| GW917 | 2.98 | 145.9 |
| GW35 | 3.469 | 25.9 |
| 66S | 0.534 | 8.7 |

The data in Table V demonstrate that the positive samples (GW917 and GW35) were well separated from the negative sample (66S), and that the equivocal sample (GW22) gave a higher signal than the negative sample (66S).

EXAMPLE 8

This example illustrates the advantage of the use of phycoerythrin as a fluorophore, by comparing phycoerythrin to various other fluorophores in terms of the signal-to-noise ratio, i.e., the signal of the positive serum to that of the negative serum. This ratio is a measure of the ability of a fluorophore to produce an analyte-specific signal.

In these experiments, a serum sample (100 μL of a 1:30 dilution) containing HSV2 was contacted with SINTEF particles (100 μL, 10 μm in diameter, magnetic and porous) coated with HSV2 antigen, and the particles are then washed. The washed particles were then resuspended, and anti-human IgG labelled with fluorophore (200 μL) was added. The particles were then read on a flow cytometer. Three groups of comparisons were made, and the results are shown in Table VI below.

TABLE VI

Fluorophore Comparisons

| Comparison No. | Fluorophore | Signal/Noise Ratio |
|---|---|---|
| 1 | fluorescein | 1.8 |
|   | phycoerythrin | 9.4 |
| 2 | bodipy TMR-X | 1.9 |
|   | tetramethylrhodamine | 1.7 |
|   | phycoerythrin | 10.7 |
| 3 | oregon green | 1.8 |
|   | PyMPO | 1.4 |
|   | phycoerythrin | 11.5 |

The higher signal-to-noise ratio of phycoerythrin relative to each of the other fluorophores is clear from each comparison.

EXAMPLE 9

This example illustrates the relationship between various characteristics of the particle and the degree of autofluorescence created by the particle. The particles were poly(styrene-co-divinylbenzene) and the characteristics that were varied include porosity vs. smoothness, diameter, percent divinylbenzene (DVB) content, and percent magnetite content. The results in terms of relative linear fluorescence units (RLFU) are listed in Table VII below.

TABLE VII

Autofluorescence vs. Various Particle Parameters

| Particle No. | Porous/-smooth | Diameter (μm) | % DVB | % Magnetite | RLFU |
|---|---|---|---|---|---|
| 1 | porous | 10.0 | n/a | 17.9 | 13.6 |
| 2 | smooth | 10.0 | n/a | 0 | 6.9 |
| 3 | smooth | 7.0 | 5 | 0 | 6.6 |
| 4 | smooth | 7.0 | 40 | 0 | 6.3 |
| 5 | smooth | 7.0 | 60 | 0 | 6.3 |
| 6 | porous | 4.2 | 37 | 0 | 6.9 |
| 7 | porous | 4.2 | 50 | 0 | 9.9 |
| 8 | porous | 15.0 | 50 | 0 | 27.6 |
| 9 | porous | 15.0 | 80 | 0 | 61.2 |
| 10 | smooth | 7.0 | 2 | 0 | 4.0 |
| 11 | smooth | 7.1 | n/a | 5 | 10.0 |
| 12 | smooth | 2.8 | n/a | 24 | 33.5 |
| 13 | smooth | 4.5 | n/a | 24.5 | 63.8 |
| 14 | porous | 4.5 | n/a | 10.5 | 30.9 |
| 15 | smooth | 1.9 | n/a | 20 | 7.1 |
| 16 | smooth | 3.18 | n/a | 12 | 8.2 |
| 17 | smooth | 4.35 | n/a | 12 | 10.0 |
| 18 | smooth | 7.1 | n/a | 5 | 16.7 |

These data indicate that smooth particles exhibit less autofluorescence than porous particles. Furthermore, for smooth particles there is little difference in autofluorescence with increasing amounts of divinylbenzene, whereas for porous particles, autofluorescence increases with increasing amounts of divinylbenzene. Magnetic particles exhibit higher autofluorescence than non-magnetic particles, and for smooth particles increasing the particles size produces an increase in autofluorescence.

The foregoing is offered primarily for purposes of illustration. It will be readily apparent to those skilled in the art that the operating conditions, materials, procedural steps and other parameters described herein may be further modified or substituted in various ways without departing from the spirit and scope of the invention.

We claim:

1. A method for individually detecting a plurality of analytes in a single fluid biological sample by assays that include the binding of said analytes in said biological sample to a solid phase that is in contact with a liquid medium in which said solid phase is insoluble, the separation of said solid phase from said liquid medium and the use of a label, said plurality of analytes comprising serum IgG antibodies to Toxoplasma gondii, Rubella virus, Cytomegalovirus, and Herpes Simplex Virus, said method comprising:
   using as said solid phase a plurality of microparticles of magnetically responsive material each with an assay reagent coupled thereto that is selectively active in an assay for one of said analytes, said microparticles classifiable into groups differing by the value of at least one selected differentiation parameter whose value is detectable, each group distinguishable from other groups by the value of said parameter and by the assay reagent coupled to the microparticles of said group;
   magnetically separating microparticles in all of said groups from said liquid medium; and
   defining said liquid medium as a first liquid medium, resuspending said microparticles separated therefore in a second liquid medium, analyzing said microparticles in said second liquid medium by flow cytometry in accordance with both the value of said selected differentiation parameter and said plurality of assays, thereby achieving individual detection of said analytes in said biological sample.

2. A method in accordance with claim 1 in which the microparticles coupled to each binding species being distinguishable from microparticles coupled to other binding species by two or more parameters that are detectable by flow cytometry and by the binding species coupled thereto.

3. A method in accordance with claim 1 in which the microparticles coupled to each binding species being distinguishable from microparticles coupled to other binding species by two or more parameters other than size that are detectable by flow cytometry and by the binding species coupled thereto, at least one of said parameters being selected from fluorescence, light scatter, light emission and absorbance.

4. A method in accordance with claim 1 in which the microparticles coupled to each binding species being distinguishable from microparticles coupled to other binding species by three or more parameters that are detectable by flow cytometry and by the binding species coupled thereto.

5. A method in accordance with claim 1 in which at least one of said assay reagents coupled to said solid phase is a binding protein specific for one of said analytes, said method includes adding to said first liquid medium a detectable label that binds to said solid phase, and said magnetic separation comprises separating detectable label that is bound to said solid phase from unbound detectable label that is suspended in said first liquid medium.

6. A method in accordance with claim 5 in which said detectable label is added to said first liquid medium as a conjugate with an additional quantity of said one analyte, causing said conjugate and said one analyte in said sample to compete for said binding protein in a competitive assay.

7. A method in accordance with claim 5 in which said detectable label is added to said first liquid medium or said second liquid medium as a conjugate with an additional quantity of said one analyte after a first incubation period, causing said conjugate to react with those sites of said at least one binding protein not occupied by said one analyte in said sample in a sequential assay.

8. A method in accordance with claim 5 in which said at least one binding protein is defined as a first binding protein, and said detectable label is added to said first liquid medium as a conjugate with a second binding protein that is also specific for said one analyte, causing said one analyte to bind to both said first binding protein and said conjugate in a sandwich assay.

9. A method in accordance with claim 8 in which said one analyte is an antigen, said first binding protein is a first antibody to said antigen, and said second binding protein is a second antibody to said antigen.

10. A method in accordance with claim 1 in which one of said assay reagents is an antigen bound to said solid phase and specific for one of said analytes in said first liquid medium which is an antibody of a selected immunoglobulin class, and said separation comprises separating said microparticles with said one analyte bound thereto from antibodies of said selected immunoglobulin class other than those specific for said bound antigen, in said first liquid medium prior to contacting said microparticles with a second liquid medium containing a detectable label that binds to all members of said selected immunoglobulin class.

11. A method in accordance with claim 1 in which said plurality of analytes comprises serum IgG antibodies to Toxoplasma gondii, Rubella virus, Cytomegalovirus, and Herpes Simplex Virus Types I and II.

12. A method in accordance with claim 1 in which analysis of said microparticles is performed by fluorescence detection.

13. A method in accordance with claim 1 in which said analytes in said assays are detected by the use of a phycoerythrin-labeled binding member and analysis of said microparticles is performed by detection of fluorescence of said phycoerythrin label.

14. A method in accordance with claim 1 in which the diameter of said microparticles is from about 0.3 micrometers to about 100 micrometers.

15. A method in accordance with claim 1 in which the diameter of said microparticles is from about 0.5 micrometers to about 40 micrometers.

16. A method in accordance with claim 1 in which said at least one selected differentiation parameter comprises fluorescence decay time, and differentiation among said groups is performed by time-resolved fluorescence detection.

17. A method in accordance with claim 1 in which said at least one selected differentiation parameter comprises degree of light scatter.

18. A method in accordance with claim 1 in which said at least one selected differentiation parameter comprises intensity of fluorescence.

19. A method in accordance with claim 1 in which said at least one selected differentiation parameter comprises a combination of forward light scatter, lateral light scatter, and fluorescence intensity at a plurality of wavelengths.

20. A method in accordance with claim 1 in which said at least one selected differentiation parameter comprises absorbance.

21. A method in accordance with claim 1 in which said microparticles are comprised of a combination of a polymer and a paramagnetic substance.

22. A composition comprising a plurality of solid-phase assay reagents selectively active in a plurality of assays each for a different analyte, said different analytes comprising serum IgG antibodies to Toxoplasma gondii, Rubella virus, Cytomegalovirus, and Herpes Simplex Virus, each said solid-phase assay reagent comprising a binding species that is selectively active in a single assay and coupled to one of a plurality of microparticles of magnetically responsive material, said microparticles classifiable into groups differing by the value of at least one selected differentiation parameter whose value is detectable, each group distinguishable from other groups by the value of said parameter and by the assay reagent coupled to the microparticles of said group, said microparticles being suitable for use in a multiplex assay procedure that includes the use of flow cytometry.

23. A composition according to claim 22 in which the analytes comprise serum IgG antibodies to Toxoplasma gondii, Rubella virus, Cytomegalovirus, and Herpes Simplex Virus Types I and II.

24. A composition in accordance with claim 22 in which the at least one differentiation parameter is one or more differentiation parameters selected from fluorescence, light scatter, light emission, and absorbance.

25. A composition in accordance with claim 22 in which the at least one differentiation parameter is one or more fluorescence parameters.

26. A composition in accordance with claim 22 in which two or more different fluorochromes are incorporated into each group of microparticles.

27. A composition in accordance with claim 22 in which the microparticles coupled to each binding species are distinguishable from microparticles coupled to other binding species by fluorescence and by at least one parameter selected from light scatter, light emission and absorbance.

28. A composition in accordance with claim 22 in which the microparticles coupled to each binding species are distinguishable from microparticles coupled to other binding species by two or more parameters that are detectable by flow cytometry and by the binding species coupled thereto.

29. A composition in accordance with claim 22 in which the microparticles coupled to each binding species are distinguishable from microparticles coupled to other binding species by two or more parameters that are detectable by flow cytometry and by the binding species coupled thereto, at least one of said parameters being selected from fluorescence, light scatter, light emission and absorbance.

30. A composition in accordance with claim 22 in which the microparticles coupled to each binding species are distinguishable from microparticles coupled to other binding species by three or more parameters that are detectable by flow cytometry and by the binding species coupled thereto.

31. A composition in accordance with claim 22 in which the diameter of the microparticles is from about 0.3 micrometers to about 100 micrometers.

32. A composition in accordance with claim 22 in which the diameter of the microparticles is from about 0.5 micrometers to about 40 micrometers.

33. A composition in accordance with claim 22 in which the microparticles are macroporous microparticles.

34. A composition in accordance with claim 22 in which said microparticles have a porosity substantially less than macroporous.

35. A composition in accordance with claim 22 in which said microparticles are comprised of a combination of a polymer and a paramagnetic substance.

36. A composition in accordance with claim 35 in which said paramagnetic substance is a metal oxide.

37. A composition in accordance with claim 35 in which said polymer is formed from monomers including carboxylate groups to permit covalent bonding of assay binding members at the microparticle surface.

38. A composition in accordance with claim 22 in which the microparticles are comprised of from about 1% to about 75% by weight of magnetically responsive material.

39. A composition in accordance with claim 22 in which the microparticles are comprised of from about 2% to about 50% by weight of magnetically responsive material.

40. A composition in accordance with claim 22 in which the microparticles are comprised of from about 3% to about 25% by weight of magnetically responsive material.

41. A composition in accordance with claim 22 in which the micromparticles are comprised of from about 5% to about 15% by weight of magnetically responsive material.

* * * * *